United States Patent [19]

Toy et al.

[11] 4,076,746

[45] Feb. 28, 1978

[54] PROCESS FOR PREPARING DIALKYL AND DIARYL PHOSPHONOTHIOIC HALIDES

[75] Inventors: Arthur D. F. Toy, Stamford, Conn.;
Eugene H. Uhing, Ridgewood, N.J.

[73] Assignee: Stauffer Chemical Company, Westport, Conn.

[21] Appl. No.: 694,270

[22] Filed: Jun. 9, 1976

Related U.S. Application Data

[63] Continuation of Ser. No. 502,702, Sept. 3, 1974, abandoned.

[51] Int. Cl.² ............................................. C07F 9/04
[52] U.S. Cl. .............................. 260/543 P; 260/125; 424/315
[58] Field of Search ........................... 260/543 P, 125

[56] References Cited

U.S. PATENT DOCUMENTS

| 2,449,933 | 9/1948 | Giammaria | 260/543 P |
| 2,993,929 | 7/1961 | Rattenbury | 260/543 P |

*Primary Examiner*—Norman Morgenstern
*Attorney, Agent, or Firm*—William R. Robinson

[57] ABSTRACT

Dialkyl or diaryl phosphonothioic halides are prepared by contacting an alkyl or aryl halide, respectively, with phosphorus sesquisulfide, $P_4S_3$, under at least autogenous pressure at a temperature of from about 200° to about 400° C. The compounds obtained are useful as pesticides and as intermediates in preparation of pesticides and other organo-phosphorus compounds.

6 Claims, No Drawings

PROCESS FOR PREPARING DIALKYL AND DIARYL PHOSPHONOTHIOIC HALIDES

This is a continuation, of application Ser. No. 502,702 filed Sept. 3, 1974 now abandoned.

BACKGROUND OF THE INVENTION

1. FIELD OF THE INVENTION

The present invention relates to a new and improved process for the preparation of dialkyl and diaryl phosphonothioic halides.

2. THE PRIOR ART

Dialkylphosphonothioic halides have been prepared in the past by reacting thionophosphinic acids with $PCl_5$ according to the following reaction scheme:

$$R_2P(S)OH + PCl_5 \rightarrow R_2P(S)Cl + POCl_3 + HCl. \tag{1}$$

This reaction is described in Organic Phosphorus Compounds, G. M. Kosolapoff and L. Maier, Vol. 4, p. 158 (Wiley —Interscience, 1972).

A method of preparing dialkarylthiophosphinic chlorides is described in Chemical Abstracts, Vol. 69, p. 10021 at 106875d(1968). According to this method, a mixture of white phosphorus, alkaryl halide and $CS_2$ or $PSCl_3$ is heated at 270° to 300° C. in the presence of a catalytic amount of iodine or coiodines. The dialkarylthiophosphinic chloride product is then separated from the mixture.

Dialkyl and diaryl phosphinothioic halides are useful as pesticides and as intermediates in preparation of pesticides and other organophosphorus compounds. The compounds also act as collectors and therefore can be used to increase the effectiveness of flotation of copper ores.

SUMMARY OF THE INVENTION

In accordance with the present invention, there is provided a new method for preparing compounds of the formula:

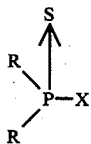

wherein R is a $C_1$–$C_{20}$ alkyl radical and the aryl (1 and 2 fused rings) substituted derivatives thereof, cycloalkyl of 5–6 carbons in the ring and aryl radicals of up to 3 fused rings or biphenyl, and the $C_1$–$C_4$ alkyl substituted derivatives of the cycloalkyl, aryl, or biphenyl groups and X is chlorine or bromine.

Typical alkyl groups include methyl, ethyl, n-propyl, isopropyl, n-butyl, isobutyl, tert-butyl, pentyl, hexyl, heptyl, octyl, nonyl, decyl, dodecyl, tetradecyl, hexadecyl, octadecyl and eicosyl. Some suitable aralkyl groups are phenylmethyl, phenylethyl, phenylbutyl, phenyloctyl, phenylhexadecyl, and the corresponding naphthyl derivatives. Ring systems wherein R is cycloalkyl having 5–6 carbons in the ring are illustrated by cyclopentyl and cyclohexyl and its derivatives.

When R is an aryl of up to and including 3 fused rings, the benzene, naphthylene and anthracene series of ring compounds are included. Examples of suitable aryls and substituted aryls are phenyl, methylphenyl, ethylphenyl, propylphenyl, butylphenyl, naphthyl, methylnaphthyl, ethylnaphthyl, propylnaphthyl, butylnaphthyl, anthryl, methylanthryl, propylanthryl, butylanthryl, dimethylphenyl, dimethylnaphthyl, diethylanthryl, and the like. Any of these radicals can contain one or more alkyl radicals and any isomeric form of said radicals can be used.

Biphenyl R groups include the $C_1$–$C_4$ alkyl substituted derivatives such as methylbiphenyl and ditolyl. There can be one or more substituents as desired and said substituents can be in any isomeric position desired. The R group can be attached to the phosphorus at a position o, m, or p to the biphenyl linkage.

With respect to X, chlorine is preferred over bromine as it is inexpensive and reacts readily. Bromine, however, can be used if it is desired to have bromine in the final compound.

The method of the present invention consists of contacting an alkyl or aryl halide reactant of the formula:

$$RX \tag{II}$$

wherein R and X are as defined above, with the phosphorus sesquisulfide reactant of the formula:

$$P_4S_3. \tag{III}$$

Representative compounds within the Formula II are methyl chloride, propyl chloride, butyl chloride, octyl chloride, decyl chloride, dodecyl chloride, hexadecyl chloride, octadecyl chloride, eicosyl chloride and the corresponding bromo- substituted derivatives; chlorocyclopentane, chlorocylohexane and the corresponding bromosubstituted derivatives; chlorobenzene, bromobenzene, chlorotoluene (chloro)ethylbenzene, (bromo)ethylbenzene, (chloro)propylbenzene, (bromo)-propylbenzene, (chloro) butylbenzene, (bromo)butylbenzene, chloronaphthylene, bromonaphthylene, (chloro)methylnaphthylene, (bromo)methylnaphthylene, (chloro)naphthylene, (bromo)ethylnaphthylene,. (chloro)propylnaphthylene, (bromo)butylnaphthylene, chloroanthracene, (chloro) methylanthracene, bromoanthracene, (chloro)butylanthracene, chlorodimethylbenzene, bromodimethylnaphthylene, chlorodiethylanthracene, and the like. In the aliphatic series above the $C_2$ alkyl and in the aromatic series, isomeric forms of the same halide compound are formed. These are intended to be included in the definition of said halide compound. The foregoing compounds are given as illustrative and in no way are considered to be inclusive of all of the alkyl and aryl halides which can be used in the method of the present invention.

The phosphorus sesquisulfide is known and can be obtained commercially.

Stoichiometrically, the process of the present invention appears to require a ratio of six moles of alkyl or aryl halide per mole of phosphorus sesquisulfide. Reactants utilized in the process of the present invention generally are employed in stoichiometric amounts, although a slight excess of either reactant can be used if desired.

A theoretical reaction scheme according to the present invention can be postulated as follows:

$$6RX + P_4S_3 \rightarrow 3R_2P(S)X + PX_3 \tag{2}$$

wherein R and X are as defined above. As this reaction scheme is postulated only, applicants do not intend to limit their process thereto. The amounts given in the theoretical scheme, however, or those closely approaching said amounts should be used for efficiency and to avoid by-product formation and the need for extensive product purification and excess reactant recovery. Other products can result from incomplete reaction, decomposition or possible equilibrium of the following type:

$$R_2P(S)X + PX_3 \rightleftarrows RP(S)X_2 + RPX_2 \qquad (III)$$

The process of the present invention is carried out at elevated temperature and at least an autogenous pressure. Temperatures of between about 200° and about 400° C. can be used although temperatures between about 250° and about 330° C. are preferred for the reaction to proceed to completion in a reasonable time. Pressures are determined by reaction temperature, the reactants, amounts of reactants used and the volume of the reaction vessel. The pressures range between about 500 to 5,000 pounds per square inch. Reaction times vary over relatively wide ranges depending upon reaction temperature and the reactivity of the alkyl or aryl halide. Generally, higher reaction temperatures require a shorter reaction time and the least reactive alkyl halides require longer reaction times. For example, methyl chloride requires a longer reaction time than the longer chain alkyl halides. Times of reaction can easily be determined by one skilled in the art. Typical reaction times are between about 1 and about 20 hours.

The process of the present invention can conveniently be effected by introducing the individual reactants into a reaction zone capable of withstanding elevated pressure, such as a metal bomb, autoclave, tube or other pressure vessel, and carrying out the reaction under at least the autogenous pressure developed by the reactants at the reaction temperature. An agitation means should be provided for said reaction zone. As the reaction is quite corrosive, especially for low molecular weight alkyl chlorides, a glass-lined reaction zone or an otherwise inert reaction zone is preferred. When aryl halides are utilized, the problem of corrosion is minimized and a metal-lined reaction zone, such as 316 stainless steel, can be used.

The products of the reaction are purified by conventional methods such as distillation, filtration, sublimation and extraction.

The identification of products is achieved by conventional methods such as elemental analysis, gas chromatography, refractive index, and nuclear magnetic resonance.

Illustrative of the compounds which can be prepared by the methods of the present invention are:
Alkyl:

$(CH_3)_2P(S)Cl$ $(CH_3)_2P(S)Br$ $(C_2H_5)_2P(S)Cl$ $(CH_2H_5)_2P(S)Br$ $(C_3H_7)_2P(S)Cl$ $(C_4H_9)_2P(S)Cl$ $(C_4H_9)_2P(S)Br$ $(C_5H_{11})_2P(S)Cl$ $(C_8H_{17})_2P(S)Cl$ $(C_8H_{17})_2P(S)Br$

CYCLIC COMPOUNDS

Benzene Series:

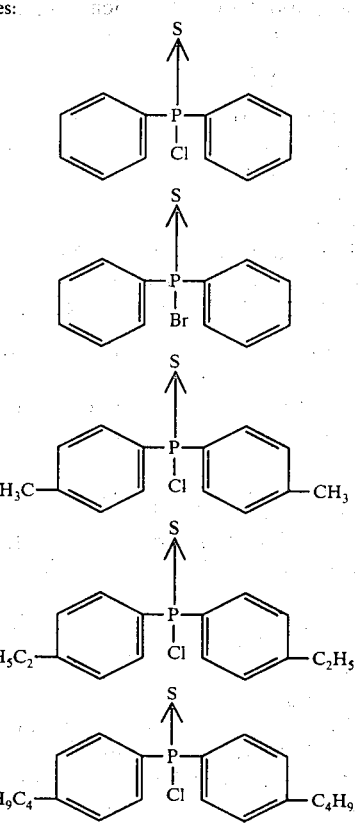

Naphthylene Series:

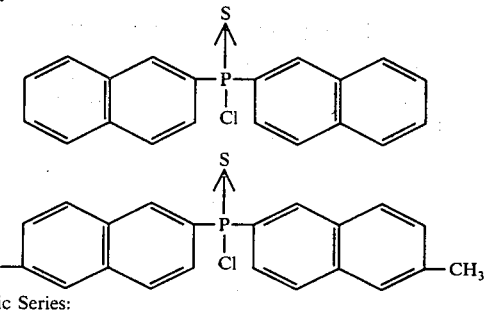

Aliphatic Series:

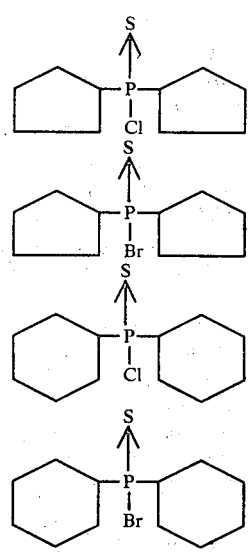

The present invention will be more fully illustrated in the examples which follow:

EXAMPLE I

In a 40 ml. glass Carius tube were placed 3.5 grams $P_4S_3$ (0.0159 mole). Then 4.2 grams $CH_3Cl$ (0.083 mole) were condensed into the Carius tube by cooling to $-70°$ C. The tube was then sealed and placed in a cold 300 ml. autoclave. Methanol, 40 ml., was placed in the autoclave to counteract pressure in the Carius tube on heat-up. After closing the autoclave, it was placed under 300 psig nitrogen pressure to counteract the pressure inside the sealed tube during initial heating. The autoclave was heated at $200°$–$210°$ C. for 12 hours. After cooling, the Carius tube was removed and opened. Almost no reaction had taken place because most of the $CH_3Cl$ was unreacted.

EXAMPLE II

Example I was repeated using 4.4 grams $P_4S_3$ (0.02 mole) and 6.0 grams $CH_3Cl$ (0.118 mole), however, the reaction temperature was $235°$–$240°$ C. for 12 hours. After cooling and opening the Carius tube, 2 grams of low boiling material evaporated ($CH_3Cl$). The remaining mixture of liquid and solid product was filtered to remove the solid material. The yield of liquid product was 2.6 grams. Analysis of the liquid product by $^{31}$P-nmr gave the following results:

| Chemical Shift from $H_3PO_4$ ppm | Compound | Mole % |
| --- | --- | --- |
| −219 | $PCl_3$ | 1.1 |
| −191.8 | $CH_3PCl_2$ | 2.6 |
| −177.3 | Unknown | 5.3 |
| −94.2 | Unknown | 12.8 |
| −86.3 | $(CH_3)_2PSCl$ | 39.5 |
| −79.9 | $CH_3PSCl_2$ | 31.9 |
| −43.8 | Unknown | 2.6 |
| −40.2 | Unknown | 0.5 |
| −23.7 | Unknown | 3.6 |

EXAMPLE III

Example II was repeated at a reaction temperature of $280°$ C. for 12 hours. The crude product obtained was filtered to give 9.2 grams of yellow liquid and 0.2 grams solid material. Analysis of the liquid product by $^{31}$P-nmr gave the following results:

| Chemical Shift from $H_3PO_4$ ppm | Compound | Mole % |
| --- | --- | --- |
| −218.3 | $PCl_3$ | 13.9 |
| −194.8 | $CH_3PCl_2$ | 7.2 |
| −92.2 | Unknown | 2.7 |
| −87.4 | $(CH_3)_2P(S)Cl$ | 59.9 |
| −81.3 | $CH_3P(S)Cl_2$ | 12.2 |
| −67.2 | Unknown | 0.9 |
| −44.3 | Unknown | 0.7 |
| −39.5 | Unknown | 0.3 |
| −23.6 | Unknown | 2.0 |

EXAMPLE IV

Example II again was repeated at $325°$ C. for 8 hours. The product was a dark liquid mixture. It was filtered to remove solids present. The yield of liquid product was 9.7 grams. Analysis by $^{31}$P-nmr gave the following results:

| Chemical Shift from $H_3PO_4$ ppm | Compound | Mole % |
| --- | --- | --- |
| −218.5 | $PCl_3$ | 15.0 |
| −194.2 | $CH_3PCl_2$ | 8.3 |
| −86.3 | $(CH_3)_2P(S)Cl$ | 63.0 |
| −80.6 | $CH_3P(S)Cl_2$ | 13.7 |

Analysis by H-nmr confirmed the major components containing methyl groups to be $(CH_3)_2P(S)Cl$ and $CH_3P(S)Cl_2$.

EXAMPLE V

In a 300 ml. 316 stainless steel autoclave, were placed 36.6 grams $P_4S_3$ (0.166 mole) and 50.5 grams $CH_3Cl$ (1.0 mole). The autoclave was heated at $250°$ C. for 12 hours. The crude product was a black paste. 100 ml. chloroform was added followed by filtration. The yield of solid material was 42 grams (about 50% starting weight). The chloroform soluble material was distilled to give 22 grams of product which by H-nmr analysis was 70% $(CH_3)_2P(S)Cl$.

EXAMPLE VI

In a 40 ml. glass Carius tube were placed 2.0 grams $P_4S_3$. (0.0091 mole) and 5.7 grams $CH_3Br$ (0.059 mole). The sealed Carius tube was placed in a 300 ml. autoclave along with 40 ml. $CH_3OH$ to equalize the pressure outside the sealed tube during heating. The autoclave was heated at $280°$ C. for 8 hours. After cooling the Carius tube to $-70°$ C., it was opened and allowed to warm to room temperature. The weight loss of vent gas was 0.5 gram. The dark liquid in the tube was filtered to remove solids present (0.8 gram). The weight of liquid product was 6.4 grams.

Analysis by H-nmr indicated the presence of 59% $(CH_3)_2P(S)Br$ and 41% $CH_3P(S)Br_2$.

EXAMPLE VII

In a 40 ml. glass Carius tube were placed 2.0 grams $P_4S_3$ (0.0091 mole) and 8.1 grams $n-C_8H_{17}Cl$ (0.055 mole). The tube was sealed and placed in an autoclave containing 40 ml. methanol. The autoclave was heated at $250°$ C. for 8 hours. After cooling, the Carius tube was found to contain a considerable amount of $P_4S_3$. The tube was placed back in the autoclave and heated at $280°$ C. for another 8 hours. After cooling, the Carius tube was opened and a light yellow liquid was removed. The yield was 8.1 grams.

Analysis by $^{31}$P-nmr gave the following results:

| Chemical Shift from $H_3PO_4$ ppm | Compound | Mole % |
| --- | --- | --- |
| −220 | $PCl_3$ | 5.7 |
| −195 | $C_8H_{17}PCl_2$ | 6.1 |
| −125 | Unknown | 2.3 |
| −116 | $(C_8H_{17}S)_3P$ | 3.4 |
| −114 | Unknown | 23.7 |
| −104 | Unknown | 4.2 |
| −102.5 | $(C_8H_{17})_2P(S)Cl$ | 30.9 |
| −89.5 | $C_8H_{17}P(S)Cl_2$ | 16.4 |
| −49.3 | $(C_8H_{17})_3P(S)$ | 5.7 |
| −45.2 | Unknown | 1.5 |

EXAMPLE VIII

In each of two 3 ml. glass Carius tubes were placed 0.44 grams $P_4S_3$ (0.002 mole) and 1.1 gram $n-C_4H_9Cl$ (0.012 mole). The tubes were sealed and placed in autoclaves containing 40 ml. methanol. Tube No. 1 was heated at 250° C. for 8 hours. Tube No. 2 was heated at 280° C. for 8 hours. After cooling, the tubes were opened and the liquid analyzed by $^{31}$P-nmr which gave the following results:

Heat at 250° C. for 8 hours: (Part A)

| Chemical Shift from $H_3PO_4$ ppm | Compound | Mole % |
|---|---|---|
| −211.3 | $C_4H_9SPCl_2$ | 21.0 |
| −201 | Unknown | 4.5 |
| −192.7 | Unknown | 1.1 |
| −188 | $(C_4H_9S)_2PCl$ | 20.1 |
| −118.9 | Unknown | 5.9 |
| −114.6 | Unknown | 3.7 |
| −104 | $(C_4H_9)_2P(S)Cl$ type isomers | 18.7 |
| −103 | Unknown | 4.2 |
| −63.7 | Unknown | 1.7 |
| −61.9 | Unknown | 3.1 |
| −53.1 | Unknown | 2.0 |
| −27.6 | Unknown | 0.8 |
| −27.3 | Unknown | 0.5 |
| +54.4 and 56.5 | Unknown | 12.5 |

Heat at 280° C. for 8 hours: (Part B)

| Chemical Shift from $H_3PO_4$ ppm | Compound | Mole % |
|---|---|---|
| −220 | $PCl_3$ | 3.7 |
| −201 | $C_4H_9PCl_2$ type isomers | 1.5 |
| −196 | $C_4H_9PCl_2$ | 4.6 |
| −177 | Unknown | 2.8 |
| −126 | $(C_4H_9)_2PCl$ | 1.5 |
| −115 | $(C_4H_9)_3P$ | 12.1 |
| −112.7 | Unknown | 7.7 |
| −105.5 | $(C_4H_9)_2P(S)Cl$ type isomers | 12.7 |
| −104.6 | $(C_4H_9)_2P(S)Cl$ type isomers | 3.3 |
| −103.7 | $(C_4H_9)_2P(S)Cl$ | 20.7 |
| −91.4 | $C_4H_9P(S)Cl_2$ | 20.9 |
| −90.4 | Unknown | 3.3 |
| −60.1 | Unknown | 1.5 |
| −50.7 | Unknown | 2.4 |
| −47.2 | Unknown | 1.1 |
| | | 99.8 |

EXAMPLE IX

In a 3 ml. glass Carius tube were placed 0.437 grams $P_4S_3$ and 1.3 grams n-$C_4H_9Br$. The sealed tube was placed in an autoclave containing 40 ml. methanol and heated at 250° C. for 8 hours. After cooling the dark liquid was removed from the tube. Analysis by $^{31}$P-nmr gave the following results:

| Chemical Shift from $H_3PO_4$ ppm | Compound | Mole % |
|---|---|---|
| −229.4 | $PBr_3$ | 22.4 |
| −192.1 | Unknown | 1.7 |
| −107.3 | Unknown | 6.2 |
| −92.0 | $(C_4H_9)_2P(S)Br$ | 35.2 |
| −65.0 | Unknown | 3.4 |
| −40.8 | $C_4H_9PSBr_2$ | 29.3 |
| −21.1 | Unknown | 1.7 |

EXAMPLE X

In a 40 ml. glass Carius tube were placed 2.2 grams $P_4S_3$ and 6.7 grams chlorobenzene ($C_6H_5Cl$). After sealing, the tube was placed in an autoclave containing 40 ml. methanol and heated at 315° C. for 12 hours. The tube was cooled and opened and the product filtered to remove traces of brown solids. The yield of light yellow colored liquid was 8.5 grams or 95.5%. The product was analyzed by $^{31}$P-nmr which gave the following results:

| Chemical Shift from $H_3PO_4$ ppm | Compound | Mole % |
|---|---|---|
| −218.2 | $PCl_3$ | 10.4 |
| −161.5 | $C_6H_5PCl_2$ | 6.4 |
| −89.7 | Unknown | 0.5 |
| −80.9 | $(C_6H_5)_2PCl$ | 1.5 |
| −79.5 | $(C_6H_5)_2P(S)Cl$ | 61.4 |
| −75.4 | Unknown | 1.0 |
| −74.4 | $C_6H_5P(S)Cl_2$ | 12.9 |
| Other peaks | Unknown | 5.9 |

EXAMPLE XI

In a 3 ml. glass Carius tube were placed 0.35 grams $P_4S_3$ and 1.5 grams bromobenzene ($C_6H_5Br$). The sealed tube was heated in an autoclave containing 40 ml. methanol at 300° C. for 12 hours. The dark liquid product was analyzed by $^{31}$P-nmr which gave the following results:

| Chemical Shift from $H_3PO_4$ ppm | Compound | Mole % |
|---|---|---|
| −229 | $PBr_3$ | 40.8 |
| −151.9 | $C_6H_5PBr_2$ | 2.3 |
| −65.9 | $(C_6H_5)_2P(S)Br$ | 35.8 |
| −19.8 | $C_6H_5P(S)Br_2$ | 18.9 |
| −10.2 | Unknown | 2.1 |
| −2.1 | Unknown | 0.2 |

EXAMPLE XII

In a 300 ml. Hastelloy C autoclave were placed 22 grams $P_4S_3$ (0.1 mole) and 67 grams of chlorobenzene ($C_6H_5Cl$) (0.6 mole). The autoclave was vented. The vent gas contained 1.1 grams HCl. The pour-out yield was 85.5 grams. The crude product was distilled and a low boiling fraction was obtained (916 grams) which assayed 42% chlorobenzene, 29% benzene and 28% $PCl_3$ by glc analysis. The second fraction had a boiling point at 70°–140° C. at 0.05 mm Hg and weighed 21.3 grams. It consisted of a mixture of $C_6H_5PCl_2$ and $C_6H_5P(S)Cl_2$. The third fraction had a boiling point at 143°–150° C. and 0.05 mm Hg. and weighed 43.4 grams. $n_D^{20} = 1.655$ (literature $n_D^{20}$ for $(C_6H_5)_2P(S)Cl = 1.6618$, 1.6628, and 1.6563). The distillation residue was 6.3 grams.

The crude product was analyzed by $^{31}$P-nmr and gave the following results:

| Chemical Shift from $H_3PO_4$ ppm | Compound | Mole % |
|---|---|---|
| −218.4 | $PCl_3$ | 7.3 |
| −161.8 | $C_6H_5PCl_2$ | 3.9 |
| −79.7 | $(C_6H_5)_2P(S)Cl$ | 56.3 |
| −76.2 | Unknown | 1.0 |
| −74.6 | $C_6H_5P(S)Cl_2$ | 19.0 |
| −46.5 | Unknown | 4.8 |
| −35.0 | Unknown | 7.8 |

The present invention is defined in the following claims.

What is claimed is:

1. A method of preparing compounds of the formula:

wherein R is selected from the group consisting of alkyl having 1 to about 20 carbon atoms, monocyclic and bicyclic fused ring aryl derivatives thereof; cycloalkyl having 5 to 6 ring carbons; aryl having up to 3 fused rings; biphenyl; and alkyl of 1 to about 4 carbon atoms, substituted derivatives of said cycloalkyl, aryl and biphenyl; and X is selected from the group consisting of chlorine and bromine, which method consists of contacting under at least an autogenous pressure at a temperature of from about 250° C. to about 330° C. a halide reactant of the formula:

RX    II

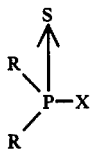

wherein R and X are as defined above, with a phosphorus sulfide reactant of the formula:

$P_4S_3.^{--}$.    III

2. The method of claim 1 wherein R is selected from the group consisting of methyl, ethyl, n-propyl, isopropyl, n-butyl, isobutyl and tert-butyl.

3. The method of claim 1 wherein X is chlorine.

4. The method of claim 1 wherein said halide reactant is selected from the group consisting of methyl chloride, methyl bromide, ethyl chloride, ethyl bromide, n-propyl chloride, n-propyl bromide, isopropyl chloride, isopropyl bromide, n-butyl chloride, n-butyl bromide, isobutyl chloride, isobutyl bromide, tert-butyl chloride and tert-butyl bromide.

5. The method of claim 1 wherein said autogenous pressure is between about 500 and 5,000 pounds per square inch absolute.

6. The method of claim 1 wherein the molar ratio of reactants is approximately 6 moles RX to 1 mole $P_4S_3$.

* * * * *